(12) United States Patent
Courbat et al.

(10) Patent No.: US 11,969,021 B2
(45) Date of Patent: *Apr. 30, 2024

(54) SYSTEMS FOR GENERATING A LIQUID AEROSOL

(71) Applicant: Altria Client Services LLC, Richmond, VA (US)

(72) Inventors: Jerome Christian Courbat, Neuchatel (CH); Oleg Mironov, Cudrefin (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/062,179

(22) Filed: Dec. 6, 2022

(65) Prior Publication Data

US 2023/0105813 A1    Apr. 6, 2023

Related U.S. Application Data

(63) Continuation of application No. 16/353,469, filed on Mar. 14, 2019, now Pat. No. 11,523,636, which is a
(Continued)

(30) Foreign Application Priority Data

Nov. 30, 2017   (EP) ..................... 17204740

(51) Int. Cl.
*A24F 40/485* (2020.01)
*A24F 40/05* (2020.01)
(Continued)

(52) U.S. Cl.
CPC ............ *A24F 40/485* (2020.01); *A24F 40/05* (2020.01); *A24F 40/30* (2020.01); *A24F 40/46* (2020.01);
(Continued)

(58) Field of Classification Search
CPC ........ A24F 40/485; A24F 40/05; A24F 40/50; A24F 40/10; A24F 40/30; A24F 40/46;
(Continued)

(56) References Cited

U.S. PATENT DOCUMENTS

| 3,232,292 A | 2/1966 | Schafer |
| 3,296,491 A | 1/1967 | Townsend |

(Continued)

FOREIGN PATENT DOCUMENTS

| CN | 201070558 Y | 6/2008 |
| CN | 105833399 A | 8/2016 |

(Continued)

OTHER PUBLICATIONS

EP Office Action dated Nov. 28, 2022 for corresponding European Patent Application No. 18803438.3.
(Continued)

*Primary Examiner* — Tu A Vo
(74) *Attorney, Agent, or Firm* — Harness, Dickey & Pierce, P.L.C.

(57) ABSTRACT

An aerosol generating system including a housing defining an airflow outlet; a liquid aerosol-forming substrate; an aerosol generator, configured to generate an aerosol from the liquid aerosol-forming substrate; a perforated plate disposed between the aerosol generator and the airflow outlet, the perforated plate defining a plurality of apertures extending through the perforated plate; and an electrode disposed between the aerosol generator and the perforated plate, wherein the perforated plate is electrically conductive, and wherein the electrode and the perforated plate are configured to generate an electrical potential.

15 Claims, 5 Drawing Sheets

Related U.S. Application Data continuation of application No. PCT/EP2018/081980, filed on Nov. 20, 2018.

(51) Int. Cl.

| | | |
|---|---|---|
| *A24F 40/10* | (2020.01) | |
| *A24F 40/30* | (2020.01) | |
| *A24F 40/46* | (2020.01) | |
| *A24F 40/50* | (2020.01) | |
| *A24F 40/90* | (2020.01) | |
| *A61M 11/00* | (2006.01) | |
| *A61M 11/02* | (2006.01) | |
| *A61M 11/04* | (2006.01) | |
| *A61M 15/00* | (2006.01) | |
| *A61M 15/02* | (2006.01) | |
| *A61M 15/06* | (2006.01) | |

(52) U.S. Cl.
CPC .............. *A24F 40/50* (2020.01); *A24F 40/90* (2020.01); *A61M 11/003* (2014.02); *A61M 11/02* (2013.01); *A61M 11/042* (2014.02); *A61M 11/044* (2014.02); *A61M 15/02* (2013.01); *A61M 15/06* (2013.01); *A24F 40/10* (2020.01); *A61M 2205/3653* (2013.01); *A61M 2205/8206* (2013.01); *A61M 2205/8237* (2013.01)

(58) Field of Classification Search
CPC ...... A24F 40/90; A61M 11/003; A61M 11/02; A61M 11/042; A61M 11/044; A61M 15/02; A61M 15/06; A61M 2205/3653; A61M 2205/8206; A61M 2205/8237
See application file for complete search history.

(56) References Cited

U.S. PATENT DOCUMENTS

| | | | | |
|---|---|---|---|---|
| 5,267,555 | A * | 12/1993 | Pajalich | ................ B05B 5/025 128/202.25 |
| 6,089,227 | A | 7/2000 | Nilsson | |
| 6,105,571 | A * | 8/2000 | Coffee | .............. A61M 15/0093 128/200.14 |
| 6,105,877 | A * | 8/2000 | Coffee | ................ A61M 15/02 239/3 |
| 6,748,944 | B1 * | 6/2004 | DellaVecchia | ....... A61M 11/001 128/202.25 |
| 6,880,554 | B1 | 4/2005 | Coffee | |
| 11,523,636 | B2 * | 12/2022 | Courbat | .............. A61M 11/044 |
| 2001/0003148 | A1 * | 6/2001 | Coffee | ................ B05B 5/0255 602/41 |
| 2006/0048772 | A1 | 3/2006 | Borgschulte | |
| 2006/0180143 | A1 | 8/2006 | Lind et al. | |
| 2008/0271732 | A1 | 11/2008 | Weaver et al. | |
| 2008/0308095 | A1 | 12/2008 | Trees et al. | |
| 2010/0083956 | A1 | 4/2010 | Fukumoto et al. | |
| 2011/0174304 | A1 | 7/2011 | Triplett, II et al. | |
| 2012/0111346 | A1 | 5/2012 | Rinker et al. | |
| 2014/0367478 | A1 | 12/2014 | Roos et al. | |
| 2017/0238611 | A1 | 8/2017 | Buchberger | |

FOREIGN PATENT DOCUMENTS

| | | | |
|---|---|---|---|
| CN | 105848504 | A | 8/2016 |
| CN | 105934171 | A | 9/2016 |
| CN | 106132222 | A | 11/2016 |
| CN | 106998816 | A | 8/2017 |
| EA | 200701646 | A1 | 2/2008 |
| EP | 2888963 | A1 | 7/2015 |
| EP | 3188570 | A2 | 7/2017 |
| EP | 3200559 | A2 | 8/2017 |
| FI | 84886 | B | 10/1991 |
| GB | 2334461 | A | 8/1999 |
| KR | 10-2017-0129710 | A | 11/2017 |
| RU | 2051755 | C1 | 1/1996 |

OTHER PUBLICATIONS

Office Action dated Mar. 1, 2023 for corresponding Chinese Patent Application No. 201880073090.3.
International Search Report PCT/ISA/210 for International Application No. PCT/EP2018/081980 dated Feb. 20, 2019.
Written Opinion of the International Searching Authority PCT/ISA/237 for International Application No. PCT/EP2018/081980 dated Feb. 20, 2019.
European Search Report for European Patent Applicaito No. 17204740 dated Sep. 4, 2018.
International Preliminary Report on Patentability and Written Opinion for corresponding Application No. PCT/EP2018/081980, dated Jun. 11, 2020.
Russian Search Report for Russian Patent Applicaiton No. 2020117405 dated Dec. 20, 2021.
Russian Office Action for Russian Patent Applicaiton No. 2020117405 dated Dec. 20, 2021.
Russian Office Action dated May 20, 2022 for corresponding Russian Patent Application No. 2020117405.
Brazilian Office Action dated Jul. 21, 2022 for corresponding Brazilian Patent Application No. 1120200071102.
Russian Notice of Allowance dated Oct. 2022 for corresponding Russian Patent Application No. 2020117405.
Office action dated Apr. 28, 2022 for corresponding U.S. Appl. No. 16/353,469.
Notice of Allowance dated Aug. 19, 2022 for corresponding U.S. Appl. No. 16/353,469.
Japanese Notice of Allowance dated Nov. 14, 2022 for corresponding Japanese Patent Application No. 2020-524476.
CN Office Action dated Jan. 31, 2023 for corresponding Chinese Patent Application No. 201880073090.3.
Notice of Allowance dated Jun. 7, 2023 for corresponding Korean Patent Application No. 2020-7010957.
Notice of Allowance for Korean Application No. 2020-7010957 dated Dec. 18, 2023.

* cited by examiner

SYSTEMS FOR GENERATING A LIQUID AEROSOL

CROSS-REFERENCE TO RELATED APPLICATIONS

The present application is a continuation of and claims priority under 35 U.S.C. § 120 to U.S. patent application Ser. No. 16/353,469, filed on Mar. 14, 2019, which claims priority to, international application number PCT/EP2018/081980, filed on Nov. 20, 2018, which claims priority to European patent application number 17204740.9, filed on Nov. 30, 2017, the entire contents of each of which are incorporated herein by reference.

FIELD

Example embodiments relate to aerosol-generating systems including a perforated plate disposed between an aerosol generator and an airflow outlet. The example embodiments also relate to aerosol-generating systems including and aerosol charging circuit including an electrode arranged for fluid communication with an aerosol.

DESCRIPTION OF RELATED ART

Devices for generating aerosols are known in the art. Such systems typically heat a liquid to vaporise the liquid and produce an aerosol. Such devices typically include a liquid storage portion or reservoir for holding a supply of a liquid aerosol forming substrate, or "e-liquid", and a heater for heating the e-liquid to generate an aerosol. Such devices also include an airflow path in communication with the heater so that the aerosol can be conveyed along the airflow path and exit the device.

The quality of the aerosol generated by known devices can be assessed using a number of different factors. Factors may include quantity of aerosol generated, density of droplets within the aerosol, temperature of the aerosol and speed of delivery of the aerosol.

SUMMARY

At least one example embodiment relates to an aerosol generating system.

In one embodiment, the aerosol generating system including a housing defining an airflow outlet; a liquid aerosol-forming substrate; an aerosol generator, configured to generate an aerosol from the liquid aerosol-forming substrate; a perforated plate disposed between the aerosol generator and the airflow outlet, the perforated plate defining a plurality of apertures extending through the perforated plate; and an electrode disposed between the aerosol generator and the perforated plate, wherein the perforated plate is electrically conductive, and wherein the electrode and the perforated plate is configured to generate an electrical potential.

In one embodiment, the perforated plate consists of a first plurality of parallel filaments and a second plurality of parallel filaments, the first plurality of filaments orthogonal to the second plurality of filaments so that the plurality of apertures is a grid of apertures.

In one embodiment, the electric potential difference between the electrode and the perforated plate is between 0.5 kilovolts and 30 kilovolts.

In one embodiment, the spacing between the electrode and the perforated plate is between 1 millimetre and 50 millimetres.

In one embodiment, the aerosol generating system further including a control circuit connected to the perforated plate and configured to allow measurement of an electrical current flowing in the perforated plate during use.

In one embodiment, the aerosol generating system including a housing defining an airflow outlet; a liquid aerosol-forming substrate; a power supply; a controller; an aerosol generator configured to generate an aerosol from the liquid aerosol-forming substrate; an aerosol charging circuit including a circuit ground and an electrode arranged for fluid communication with aerosol generated by the aerosol generator, wherein the controller is configured to control a supply of electrical power from the power supply to the electrode to charge the electrode to a potential difference of between 0.5 kilovolts and 30 kilovolts with respect to the circuit ground; and a perforated plate disposed between the electrode and the airflow outlet, the perforated plate defining a plurality of apertures extending through the perforated plate.

In one embodiment, the electrode is a nozzle configured to direct aerosol to the airflow outlet.

In one embodiment, the separation between the electrode and the perforated plate is between 1 millimetre and 50 millimetres.

In one embodiment, the perforated plate is electrically connected to the circuit ground.

In one embodiment, the controller is connected to the perforated plate and configured to allow measurement of an electrical current flowing in the perforated plate during use.

In one embodiment, the perforated plate consists of a first plurality of parallel filaments and a second plurality of parallel filaments, the first plurality of filaments orthogonal to the second plurality of filaments so that the plurality of apertures is a grid of apertures.

In one embodiment, the aerosol generating system further including a first reservoir containing the liquid aerosol-forming substrate and a second reservoir containing an ionizable liquid.

In one embodiment, the electrode is two coaxial nozzles including a first nozzle configured to eject liquid aerosol-forming substrate from the first reservoir and a second nozzle configured to eject ionizable liquid from the second reservoir.

BRIEF DESCRIPTION OF THE DRAWINGS

Features described in relation to one example embodiment may also be applicable to other example embodiments. Example embodiments will now be described, by way of example only, with reference to the figures.

DETAILED DESCRIPTION

Figure 1:
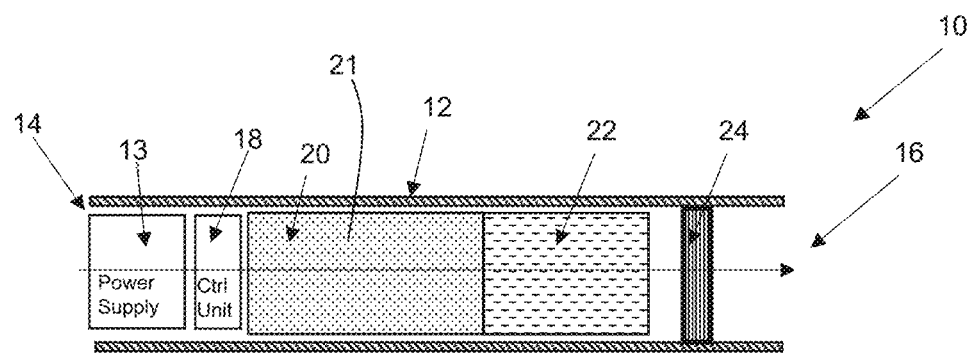
FIG. 1 illustrates a schematic representation of a first embodiment of an aerosol generating system, in accordance with an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, elements, regions, layers and/or sections, these elements, elements, regions, layers, and/or sections should not be limited by these terms. These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

General Methodology

It would be desirable to provide an aerosol-generating system that facilitates delivery of an aerosol that may provide an improved adult vaper's experience. It would be desirable to provide an aerosol-generating system that facilitates consistent delivery of an aerosol.

Specific Example Embodiments

According to a first aspect of the example embodiments there is provided an aerosol generating system including a housing defining an airflow outlet, and a liquid aerosol-forming substrate. The system also includes an aerosol generator configured to form an aerosol from the liquid aerosol-forming substrate, and a perforated plate disposed between the aerosol generator and the airflow outlet. The perforated plate defines a plurality of apertures extending through the perforated plate.

As used herein, the term ‘aerosol-forming substrate’ relates to a substrate capable of releasing volatile compounds that can form an aerosol. Such volatile compounds may be released by heating the aerosol-forming substrate or other aerosolising means. A suitable substrate could be in liquid form, such as an e-liquid.

The present inventors have recognised that a property of an aerosol that may affect an adult vaper’s experience is the average droplet size of the aerosol. In particular, the present inventors have recognised that an aerosol including an average droplet size that is too large may adversely affect an adult vaper’s experience.

Aerosol-generating systems according to the example embodiments include a perforated plate between an aerosol generator and an airflow outlet. Therefore, during use, aerosol produced by the aerosol generator must pass through the perforated plate before it can be inhaled. Any droplets of the aerosol that are larger than the apertures in the perforated plate may be prevented from passing through the perforated plate. Therefore, the perforated plate may be configured to limit the maximum droplet size of the aerosol delivered. For example, a droplet of the aerosol that is larger than an aperture in the perforated plate can be blocked by the plate that defines each aperture.

Controlling the maximum droplet size of an aerosol that is generated by the aerosol generating system may allow the perforated plate to facilitate consistent delivery of an aerosol. The consistent droplet size of aerosols delivered by aerosol generating systems according to the example embodiments provides a consistent adult vaper experience.

The perforated plate may include a sheet material including the plurality of apertures extending through the sheet material. The sheet material may be a single element. The plurality of apertures may be formed in the sheet material using any suitable process. The plurality of apertures may be formed using at least one of drilling, punching, laser perforation, and electron discharge machining.

The perforated plate may include a composite structure, formed of multiple elements that together define a plurality of openings extending through the structure, wherein the plurality of openings form the plurality of apertures. The perforated plate may include a plurality of elongate elements connected to form a planar composite structure. The perforated plate may include an array of filaments or threads, wherein each of the plurality of apertures is formed by an opening defined between consecutive filaments or threads.

The array of filaments may be formed of a plurality of parallel filaments defining elongate apertures therebetween. As used, herein, the term "parallel" means substantially parallel, within plus or minus 10 degrees, or within plus or minus 5 degrees. The array of filaments may be formed of a first plurality of parallel filaments, and a second plurality of parallel filaments, the first plurality of filaments orthogonal to the second plurality of filaments. The plurality of apertures may be a grid of apertures. The first plurality of parallel filaments and the second plurality of parallel filaments may lie within a single plane.

Each of the filaments that forms the perforated plate may have a maximum thickness of between about 10 micrometres and about 500 micrometres. Providing filaments having a maximum thickness within this range may block some droplets of aerosol.

The perforated plate may include a mesh.

The aerosol generator may include a heater. During use, the heater vaporises liquid aerosol forming substrate. The heater may be an electric heater.

The heater may be a resistive heater.

The heater may be an inductive heater. The aerosol generator may further include a susceptor, wherein the inductive heater is configured to inductively heat the susceptor during use. The inductive heater may be positioned around a portion of the susceptor.

The aerosol generating system may include a reservoir containing the liquid aerosol-forming substrate. The reservoir may be disposed within the housing.

The aerosol generator may be positioned at an outlet of the reservoir. The aerosol generating system may include a liquid transfer element arranged to transfer liquid aerosol-forming substrate from the reservoir to the aerosol generator. The liquid transfer element may include at least one of a wick or a capillary tube.

The aerosol generator may include a nozzle assembly. During use, droplets of liquid aerosol-forming substrate from the reservoir are ejected through the nozzle. The aerosol generator may include a piezoelectric component. During use, the piezoelectric component ejects droplets of liquid aerosol-forming substrate through the nozzle. The nozzle is in fluid communication with the reservoir. The nozzle may form part of the reservoir. The piezoelectric component may be positioned inside the reservoir. The aerosol generator may include a mesh covering an outlet of the nozzle. During use, liquid aerosol-forming substrate passes through the mesh as droplets of liquid aerosol-forming substrate are ejected from the nozzle outlet.

Each aperture of the perforated plate may have a maximum width within a plane defined by the perforated plate. The maximum width of each aperture may be between about 10 micrometres and about 100 micrometres. Aerosol droplets with a diameter larger than about 100 micrometres may be removed or resized into smaller droplets by apertures having a maximum width of less than about 100 micrometres. Apertures having a maximum width of greater than about 10 micrometres may facilitate sufficient airflow through the perforated plate to reduce or minimise the condensation of aerosol droplets on the perforated plate.

Each of the apertures may be substantially square or substantially rectangular.

The housing may define an airflow channel extending between the aerosol generator and the airflow outlet. The perforated plate may extend across the airflow channel. The perforated plate helps ensure that, during use, the aerosol generated by the aerosol generator passes through the perforated plate before the aerosol is inhaled via the airflow outlet. The perforated plate may define a plane, wherein the plane extends orthogonally with respect to a longitudinal axis of the airflow channel. The plane may extend orthogonally with respect to a direction of airflow through the airflow channel during use.

The aerosol generator may be arranged to direct aerosol generated by the aerosol generator towards the perforated plate. Directing the generated aerosol directly at the perforated plate may increase the speed of the aerosol droplets when they reach the perforated plate. Increasing the speed of the droplets when they encounter the perforated plate may facilitate blocking of larger droplets as they pass through the apertures in the perforated plate. Increasing the speed of the droplets may reduce or minimise the collection and build-up of droplets on the perforated plate. Increasing the speed of the droplets may reduce or minimise the need for cleaning of the aerosol-generating system.

The perforated plate may be constructed from any suitable material. The perforated plate may be formed from a polymer material. The perforated plate may be formed from a metal. Suitable metals include steels. The perforated plate may be formed from a stainless steel.

The aerosol generating system may further include an electrode disposed between the aerosol generator and the perforated plate, the electrode configured to electrostatically charge the aerosol. When an electrode is provided, the perforated plate may be electrically conductive, wherein the aerosol-generating system is configured to generate an electric potential difference between the electrode and the perforated plate. Alternatively, when an electrode is provided, the perforated plate may be electrically insulating.

The droplets of the aerosol generated by the aerosol generator may be electrostatically charged by the electrode such that the droplets of aerosol are electrostatically attracted to the perforated plate. The electrostatic attractive forces accelerate the droplets towards the perforated plate. Accelerating the droplets of aerosol towards the perforated plate may increase the speed of the droplets passing through the perforated plate. This increased speed of the droplets may facilitate blocking of larger droplets as they pass through the perforated plate. This blocking of larger droplets may reduce or minimise the collection and build-up of droplets on the perforated plate. These reduced or minimized collection and build-up of droplets may reduce or minimise the need for cleaning of the aerosol-generating system.

The aerosol generating system may be configured to generate an electric potential difference between the electrode and the perforated plate of between about 0.5 kilovolts and about 50 kilovolts, between about 5 kilovolts and about 15 kilovolts, or about 10 kilovolts. At the typical dimensions of an aerosol-generating system, an electric potential difference below about 50 kilovolts may be insufficient to cause breakdown of the air within the system. An electrical potential difference above 0.5 kilovolts may be strong enough to provide sufficient acceleration of the charged droplets of aerosol towards the perforated plate. The potential difference may be provided with the use of a transformer within the aerosol generating system. The potential difference may be provided with the use of at least one boost converter.

As pacing between the electrode and the perforated plate is between about 1 millimetre and about 50 millimetres, or between about 3 millimetres and about 10 millimetres. Spacings within these ranges may reduce or minimise the risk of electrical breakdown of the air within the system, particularly when combined with the ranges of electric potential difference defined herein. Spacings within the range of between about 3 millimetres and about 10 millimetres may allow construction of the aerosol-generating system with a size that more closely resembles a cigarette. An aerosol generating system having a size that is similar to the size of a cigarette may allow the aerosol-generating system to be easily stored or transported in a similar manner to a cigarette.

The perforated plate may be grounded with respect to the electrode. Grounding the perforated plate may allow aerosol droplets that have been charged by the electrode to release their charge to the perforated plate. Grounding the perforated plate may allow the aerosol droplets delivered to be neutral or not charged.

The perforated plate may not be grounded with respect to the electrode, such that the aerosol droplets retain their charge as they pass through the apertures in the perforated plate and charged aerosol droplets are delivered.

The aerosol generating system may further include a control circuit.

In example embodiments in which the aerosol generator includes at least one of an electric heater and a piezoelectric component, the control circuit may be configured to control a supply of electrical power to the electric heater, the piezoelectric component, or both.

In example embodiments in which the aerosol-generating system include an electrode, the control circuit may be configured to control a supply of electrical power to the electrode to generate an electric potential different between the electrode and the perforated plate. The control circuit may be configured to control a supply of electrical power to the perforated plate to facilitate the generation of an electric potential difference between the electrode and the perforated plate. The control circuit may be connected to the perforated plate and configured to measure an electrical current in the perforated plate during use. Measuring the electrical current in the perforated plate may provide an indication of a flow rate of aerosol through the perforated plate. In other words, charged droplets of aerosol incident on the perforated plate may generate an electrical current within the perforated plate. The rate at which charged droplets pass through the array will vary the electrical current measured in the perforated plate. Measuring an electrical current within the perforated plate during use may allow the control circuit to estimate an amount of aerosol delivered. An estimation of an amount of aerosol generated may allow the operation and efficiency of the aerosol generating system over time to be monitored. For example, an estimate of an amount of aerosol generated may be used to estimate an amount of liquid aerosol-forming substrate remaining in the aerosol generating system.

The liquid aerosol-forming substrate may include water.

The liquid aerosol-forming substrate may include an aerosol-former. As used herein, the term "aerosol-former" refers to any suitable known compound or mixture of compounds that, in use, facilitates formation of a dense and stable aerosol. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Example aerosol formers are polyhydric alcohols or mixtures thereof, such as triethylene glycol, 1,3-butanediol and, glycerine or polyethylene glycol.

The liquid aerosol-forming substrate may include at least one of nicotine or a tobacco product. Additionally, or alternatively, the liquid aerosol-forming substrate may include another target compound for delivery. In example embodiments in which the liquid aerosol-forming substrate includes nicotine, the nicotine may be included in the liquid aerosol-forming substrate with an aerosol-former.

The aerosol-generating system may include an airflow inlet. The airflow inlet is in fluid communication with the aerosol generator. During use, air enters the aerosol-generating system through the airflow inlet and exits the aerosol-generating system through the airflow outlet.

The aerosol-generating system may include at least one power supply. In example embodiments in which the aerosol generator includes at least one of an electric heater and a piezoelectric component, the at least one power supply may be configured to provide a supply of electrical power to the electric heater, the piezoelectric component, or both.

In example embodiments in which the aerosol-generating system includes an electrode, the at least one power supply may be configured to provide a supply of electrical power to the electrode to generate an electric potential different between the electrode and the perforated plate. The at least one power supply may be configured to provide a supply of electrical power to the perforated plate to facilitate the generation of an electric potential difference between the electrode and the perforated plate.

The at least one power supply may include a first power supply configured to provide a supply of electrical power to the aerosol generator and a second power supply configured to provide a supply of electrical power to the electrode.

In example embodiments in which the aerosol-generating system includes a control circuit, the control circuit may be configured to control a supply of electrical power from the at least one power supply to at least one of the aerosol generator, the electrode and the perforated plate.

The at least one power supply may include a battery, such as a rechargeable lithium ion battery. The at least one power supply may include another form of charge storage device such as a capacitor. The at least one power supply may require recharging. The at least one power supply may have a capacity that allows for the storage of enough energy for one or more uses of the aerosol generating system. For example, the at least one power supply may have sufficient capacity to allow for the continuous generation of aerosol for a period of around six minutes, corresponding to the typical time taken to smoke a cigarette, or for a period that is a multiple of six minutes. In another example, the at least one power supply may have sufficient capacity to allow for a predetermined number of puffs or discrete activations.

Some aspects or components of the aerosol generating system may be separable, removable, or single-use and disposable. The system is configured for use to produce an inhalable aerosol when fully assembled, as further described herein. The aerosol generating system may include a power supply section and an aerosol generating section configured for attachment to the power supply section. In example embodiments in which the aerosol generating system includes at least one of a power supply and a control circuit, the power supply and the control circuit may be positioned in the power supply section. The liquid aerosol-forming substrate and the airflow outlet may be provided in the aerosol generating section. The aerosol generator and the perforated plate may each form part of the power supply section or the aerosol generating section.

According to a second aspect of the example embodiments there is provided an aerosol generating system including a housing defining an airflow outlet; a liquid aerosol-forming substrate; a power supply; a controller; an aerosol generator configured to generate an aerosol from the liquid aerosol-forming substrate; and an aerosol charging circuit including a circuit ground and an electrode arranged for fluid communication with aerosol generated by the aerosol generator, wherein the controller is configured to control a supply of electrical power from the power supply to the electrode to charge the electrode to a potential difference of between about 0.5 kilovolts and about 30 kilovolts with respect to the circuit ground. The controller may be configured to charge the electrode to a potential difference of between about 5 kilovolts and about 15 kilovolts, or about 10 kilovolts with respect to the circuit ground.

During use, the electrode charges or ionizes droplets of the aerosol generated by the aerosol generator. Once the droplets are charged, repulsive forces are generated within the charged droplets. The electrostatic charges of each e-liquid particle within each droplet repel each other, and the surface tension acting on the outer surface of each droplet hold the droplet together. The larger a droplet is, the more e-liquid particles there are contained within the droplet, and the more repulsive electrostatic forces there are within the droplet once the droplet is charged. At what is known as the Rayleigh Limit, the internal repulsive forces overcome the surface tension forces and the droplet breaks apart into multiple smaller droplets. This process is known as Coulomb fission. The present inventors have appreciated that charging droplets of a generated aerosol such that droplets over a maximum, predetermined size reach their Rayleigh Limit and break apart into smaller droplets provides a reliable and consistent mechanism to limit the maximum size of aerosol droplets and provide a more homogeneous aerosol. The precise value to which the droplets are charged may be chosen for a particular liquid aerosol aerosol-forming substrate. At the typical dimensions of an aerosol-generating system, an electric potential difference below about 30 kilovolts may be insufficient to cause breakdown of the air within the system.

The present inventors have recognised that an adult vaper's experience may be particularly favourable when the maximum droplet size of an aerosol is equal to or less than about 2 micrometres. The present inventors have further recognised that, for typical liquid aerosol-forming substrates, an electrical potential difference of at least about 0.5 kilovolts is sufficient to electrically charge droplets having a size of greater than about 2 micrometres to an electrical charge exceeding the Rayleigh Limit.

The potential difference may be provided with the use of a transformer within the aerosol generating system. The potential difference may be provided with the use of at least one boost converter.

The power supply may be a single power supply and the controller may be configured to control a supply of electrical power from the single power supply to the aerosol generator and the aerosol charging circuit. The power supply may include first and second power supplies, wherein the controller is configured to control a supply of electrical power from the first power supply to the aerosol generator and to control a supply of electrical power from the second power supply to the aerosol charging circuit.

The aerosol generator may include a heater. During use, the heater vaporises liquid aerosol forming substrate. The heater may be an electric heater.

The heater may be a resistive heater.

The heater may be an inductive heater. The aerosol generator may further include a susceptor, wherein the inductive heater is configured to inductively heat the susceptor during use. The inductive heater may be positioned around a portion of the susceptor.

The aerosol generating system may include a reservoir containing the liquid aerosol-forming substrate. The reservoir may be disposed within the housing.

The aerosol generator may be positioned at an outlet of the reservoir. The aerosol generating system may include a liquid transfer element arranged to transfer liquid aerosol-forming substrate from the reservoir to the aerosol generator. The liquid transfer element may include at least one of a wick or a capillary tube.

The aerosol generator may include a nozzle assembly. During use, droplets of liquid aerosol-forming substrate from the reservoir are ejected through the nozzle. The aerosol generator may include a piezoelectric component. During use, the piezoelectric component ejects droplets of liquid aerosol-forming substrate through the nozzle. The nozzle is in fluid communication with the reservoir. The nozzle may form part of the reservoir. The piezoelectric component may be positioned inside the reservoir. The aerosol generator may include a mesh covering an outlet of the nozzle. During use, liquid aerosol-forming substrate passes through the mesh as droplets of liquid aerosol-forming substrate are ejected from the nozzle outlet.

The aerosol generating system may include an internal airflow channel in fluid communication with the aerosol generator. The internal airflow channel may extend between an airflow inlet and the airflow outlet. During use, the airflow passing through the airflow channel may pick up generated aerosol as the airflow passes the aerosol generator. Airflow containing the generated aerosol may pass out of the airflow outlet. Based on the positioning of the airflow inlet and airflow outlet, the relative positioning of the elements within the aerosol generating system of the example embodiments may be defined according to whether they are upstream or downstream from other elements. The airflow inlet is upstream of the airflow outlet. The aerosol generator is downstream of the airflow inlet, and upstream of the electrode.

The electrode may be located downstream of the aerosol generator and upstream of the airflow outlet. The electrode may include at least one of a ring electrode and a mesh electrode. During use, aerosol generated by the aerosol generator may pass through the electrode.

The electrode may be a nozzle configured to direct aerosol to the airflow outlet. The nozzle may define a nozzle outlet through which the aerosol flows to the airflow outlet. The charged nozzle may create an electric field in the surrounding region. In particular, the nozzle electrode may create an electric field in the nozzle outlet. During use, the generated aerosol passes through the nozzle outlet, at which point the droplets of the aerosol are ionized. The nozzle configuration for the electrode may ensure that all droplets of the aerosol must pass close to the electrode and therefore through the electric field. The nozzle configuration may provide an efficient ionizing assembly. In example embodiments in which the aerosol generator includes a nozzle assembly, the aerosol generator nozzle and the electrode nozzle may be the same nozzle.

In example embodiments in which the aerosol generating system includes a reservoir for storing a liquid aerosol-forming substrate, the reservoir may be a first reservoir. The aerosol generating system may further include a second reservoir for an ionizable liquid. The second reservoir may contain an ionizable liquid. Some liquid aerosol-forming substrates that may be for inhalation may not be easily ionized. An ionizable liquid may be more easily ionized than a given liquid aerosol-forming substrate. An ionizable liquid may be ionized at a lower potential difference than a given liquid aerosol-forming substrate. A larger proportion of an ionizable liquid may be ionized at a given potential difference than the proportion of a given liquid aerosol-forming substrate at the same potential difference. The ionizable liquid may facilitate ionization of the liquid aerosol-forming substrate. The aerosol-generating system may be configured to combine ionizable liquid from the second reservoir with liquid aerosol-forming substrate from the first reservoir. The aerosol-generating system may be configured to combine the ionizing liquid and the liquid aerosol-forming substrate before aerosolisation of the liquid aerosol-forming substrate. The aerosol generating system may be configured to combine the ionizing liquid and the liquid aerosol-forming substrate after aerosolisation of the liquid aerosol-forming substrate and upstream of the electrode. The ionizable liquid may be at least one of aerosolisable and volatile. A suitable ionizable liquid may include ethanol.

In example embodiments in which the aerosol generator includes a nozzle assembly, the nozzle of the nozzle assembly may be formed of two coaxial nozzles. The two coaxial nozzles may include a first nozzle configured to eject liquid aerosol-forming substrate from the first reservoir and a second nozzle configured to eject ionizable liquid from the second reservoir. The two coaxial nozzles may produce coaxial streams of liquid aerosol-forming substrate and ionizable liquid, one within the other. This may encourage mixing of the liquid aerosol-forming substrate and the ionizable liquid. This may result in a more homogeneous mixture of the liquid aerosol-forming substrate and the ionizable liquid, which may facilitate charging of the droplets aerosol by the electrode.

The controller may be configured to control a supply of electrical power to at least one of the first nozzle and the second nozzle. The controller may be configured to control a same supply of electrical power to the first and second nozzles to charge the first and second nozzles to a same potential difference with respect to the circuit ground. The controller may be configured to control a different supply of electrical power to the first and second nozzles to charge the first and second nozzles to different potential differences with respect to the circuit ground. The controller may be configured to control a supply of electrical power to only one of the first and second nozzles.

The aerosol-generating system may further include an electrically conductive perforated plate positioned between the electrode and the airflow outlet. The perforated plate defines a plurality of apertures extending through the perforated plate. The charged aerosol produced by the aerosol generator and the electrode must pass through the perforated plate before the aerosol can be inhaled. Any droplets of the aerosol that are larger than the apertures defined within the perforated plate may be prevented from passing through the perforated plate. Therefore, the perforated plate may be configured to limit the maximum droplet size of the aerosol delivered.

The perforated plate may include any of the features of the perforated plate described herein with respect to the first aspect of the example embodiments.

The aerosol-generating system may be configured so that, when the electrode is charged to generate a potential difference between the electrode and the circuit ground, a potential difference is also generated between the electrode and the perforated plate. During use, the droplets of the aerosol that are electrostatically charged by the electrode may be electrostatically attracted to the perforated plate. The electrostatic attractive forces accelerate the droplets towards the perforated plate. Accelerating the droplets of aerosol towards the perforated plate may increase the speed of the droplets passing through the perforated plate. Accelerating the droplets of aerosol may facilitate blocking of larger droplets as they pass through the perforated plate. Accelerating the droplets of aerosol may reduce or minimise the collection and build-up of droplets on the perforated plate. Accelerating the droplets of aerosol may reduce or minimise the need for cleaning of the aerosol-generating system.

The controller may be configured to control a supply of electrical power to the perforated plate to facilitate the generation of an electric potential difference between the electrode and the perforated plate.

The perforated plate may be connected to or form part of the circuit ground of the aerosol charging circuit.

A spacing between the electrode and the perforated plate may be between about 1 millimetre and about 50 millimetres, or between about 3 millimetres and about 10 millimetres. Spacings within these ranges may reduce or minimise the risk of electrical breakdown of the air within the system, and the effect may be increased when combined with the ranges of electric potential difference according to the second aspect of the example embodiments. Spacings within the range of between about 3 millimetres and about 10 millimetres may allow construction of the aerosol-generating system with a size that more closely resembles a cigarette. An aerosol generating system having a size that is similar to the size of a cigarette may allow the aerosol-generating system to be easily stored or transported in a similar manner to a cigarette.

The controller may be connected to the perforated plate and configured to measure an electrical current in the perforated plate during use. Measuring the electrical current in the perforated plate may provide an indication of a flow rate of aerosol through the perforated plate. In other words, charged droplets of aerosol incident on the perforated plate may generate an electrical current within the perforated plate. The rate at which charged droplets pass through the perforated plate will vary the electrical current measured in the perforated plate. Measuring an electrical current within the perforated plate during use may allow the control circuit to estimate an amount of aerosol delivered. Estimating the amount of aerosol delivered may allow the operation and efficiency of the aerosol generating system over time to be monitored. For example, an estimate of an amount of aerosol delivered may be used to estimate an amount of liquid aerosol-forming substrate remaining in the aerosol generating system.

The perforated plate may be electrically connected to the circuit ground.

The liquid aerosol-forming substrate may include water.

The liquid aerosol-forming substrate may include an aerosol-former. As used herein, the term "aerosol-former" refers to any suitable known compound or mixture of compounds that, in use, facilitates formation of a dense and stable aerosol. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Example aerosol formers are polyhydric alcohols or mixtures thereof, such as triethylene glycol, 1,3-butanediol andglycerine or polyethylene glycol.

The liquid aerosol-forming substrate may include at least one of nicotine or a tobacco product. Additionally, or alternatively, the liquid aerosol-forming substrate may include another target compound for delivery. In example embodiments in which the liquid aerosol-forming substrate includes nicotine, the nicotine may be included in the liquid aerosol-forming substrate with an aerosol-former.

The power supply may include a first power supply configured to provide a supply of electrical power to the aerosol generator and a second power supply configured to provide a supply of electrical power to the electrode.

The power supply may include a battery, such as a rechargeable lithium ion battery. The power supply may include another form of charge storage device such as a capacitor. The power supply may require recharging. The power supply may have a capacity that allows for the storage of enough energy for one or more uses of the aerosol generating system. For example, the power supply may have sufficient capacity to allow for the continuous generation of aerosol for a period of around six minutes, corresponding to the typical time taken to smoke a cigarette, or for a period that is a multiple of six minutes. In another example, the power supply may have sufficient capacity to allow for a predetermined number of puffs or discrete activations.

Some aspects or components of the aerosol generating system may be separable, removable, or single-use and disposable. The system is configured for use to produce an inhalable aerosol when fully assembled, as further described herein. The aerosol generating system may include a power supply section and an aerosol generating section configured for attachment to the power supply section. The power supply and the controller may be positioned in the power supply section. The liquid aerosol-forming substrate and the airflow outlet may be provided in the aerosol generating section. The aerosol generator and the electrode may each form part of the power supply section or the aerosol generating section.

Example Structural Embodiments

FIG. 1 illustrates a schematic representation of a first embodiment of an aerosol generating system, in accordance with an example embodiment. The aerosol generating system 10 includes a housing 12 with an airflow inlet 14 and an airflow outlet 16. Within the housing 12 is a power supply 13 and control unit 18, a reservoir 20 of liquid aerosol-forming substrate 21, an aerosol generator 22, and a perforated plate 24.

The aerosol generator 22 in a first configuration is a tank 26, separate from the reservoir 20, but in fluid communication with the reservoir 20 so that liquid aerosol-forming substrate 21 can flow from the reservoir 20 to the tank 26 to be aerosolised. The tank 26 includes a piezoelectric component 28 and mesh 30 (see FIG. 2). Together, the piezoelectric component 28 and the mesh 30 are configured to aerosolise the liquid aerosol-forming substrate within the tank 26.

Figure 2:
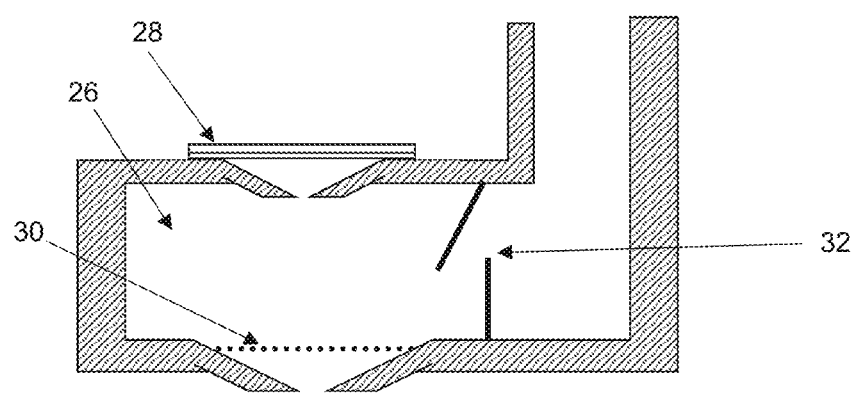
FIG. 2 illustrates an aerosol generator arrangement, in accordance with an example embodiment.

FIG. 2 illustrates an aerosol generator arrangement, in accordance with an example embodiment, When the piezoelectric component 28 is not excited, liquid aerosol-forming substrate 21 from the reservoir 20 can enter the tank 26 through a one-way valve 32.

Figure 3:
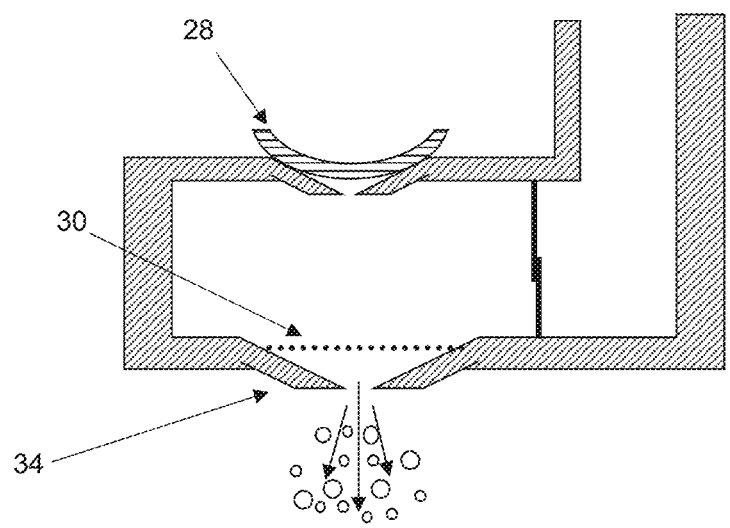
FIG. 3 illustrates an aerosol generator arrangement, in accordance with an example embodiment.

FIG. 3 illustrates an aerosol generator arrangement, in accordance with an example embodiment., When the piezoelectric component 28 is excited, the piezoelectric component 28 vibrates and compresses the liquid aerosol-forming substrate in the tank 26. The piezoelectric component 28 is excited by passing alternating electric current through the piezoelectric component 28. The electric current is provided by the power supply 13 and the control unit 18. When excited, the piezoelectric component 28 bends or flexes and the pressure in the tank 26 increases. The one-way valve 32 hinders or prevents the flow of liquid aerosol-forming substrate back through the one-way valve 32 and so the pressure within the tank 26 forces liquid aerosol-forming substrate through the mesh 30, and out through a nozzle 34 as aerosol droplets. In this way the liquid aerosol-forming substrate 21 is aerosolised.

The aerosol generator 22 in a second configuration is a heater assembly 36 configured to heat the liquid aerosol-forming substrate 21 so as to vaporise the liquid aerosol-forming substrate 21 and form an aerosol.

Figure 4:
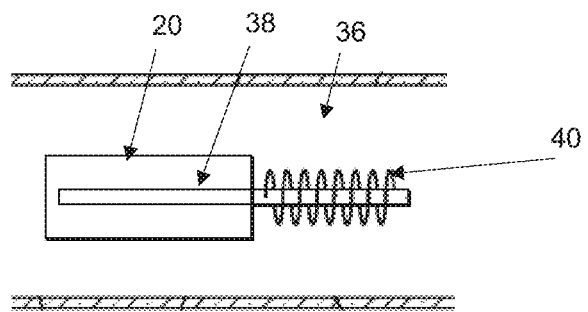
FIG. 4 illustrates a heater arrangement, in accordance with an example embodiment.

FIG. 4 illustrates a heater arrangement, in accordance with an example embodiment. The heater assembly 36 includes a wick 38 and a heater coil 40. The wick 38 extends into the reservoir 20 to wick liquid aerosol-forming substrate from the reservoir 20 to the heater coil 40. The wick 38 may be a length of absorbent material or a capillary tube to transport the liquid aerosol-forming substrate via capillary action. The heater coil 40 is powered by the power supply 13 and control unit 18. The heater coil 40 is a coil of resistive material, for example, a metal, which is resistively heated when an electrical current is passed through the heater coil 40. The power supply 13 and control unit 18 pass electrical current through the heater coil 40 to heat and volatise the liquid aerosol-forming substrate in the wick 38.

Alternatively, the heater assembly 36 could be a resistive heater in an alternative configuration, such as a resistive mesh positioned at one end or along the length of the wick. Alternatively, the heater assembly 36 could be a resistive heater in the form of a rod or blade projecting into the reservoir 20. Alternatively, the heater assembly 36 could be a combination of a susceptor in thermal contact with a wick or projecting into the reservoir 20 and an inductor coil configured to inductively heat the susceptor.

The aerosol generated by the aerosol generator 22 is picked up by airflow through the aerosol generating system 10 when air is drawn through the airflow outlet 16. The aerosol generator 22 may be controlled and powered such that aerosol is only generated when the aerosol generating system 10 is drawn upon. A pressure sensor may be incorporated into the control unit 18 to determine when the aerosol generating system 10 is drawn upon.

Both of the configurations of the aerosol generator 22 shown in FIGS. 2 to 4 may produce a wide range of droplet sizes within the generated aerosol. To homogenise the droplet sizes within the generated aerosol by removing or resizing droplets that are above a desired maximum size, in this first example embodiment of the example embodiments the aerosol generating system further includes a perforated plate 24 between the aerosol generator 22 and the airflow outlet 16. During use, aerosol generated by the aerosol generator 22 flows towards the perforated plate 24. The perforated plate 24 includes a plurality of apertures 54 extending through the perforated plate 24. The apertures 54 are about 10 micrometres in diameter. The perforated plate 24 is configured to remove or resize droplets with a diameter over 10 micrometres.

Figure 5:
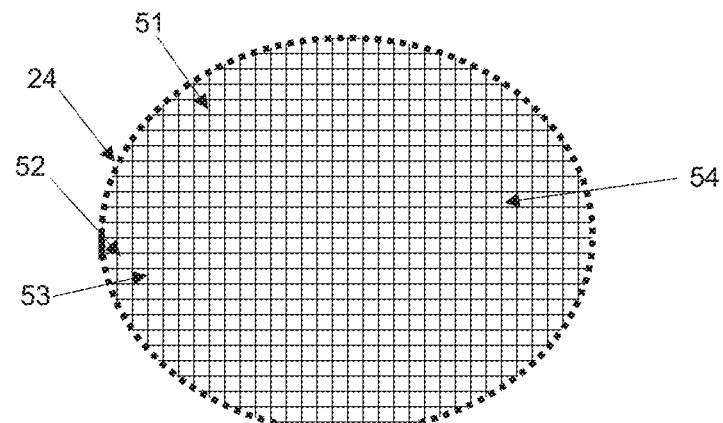
FIG. 5 illustrates a perforated plate, in accordance with an example embodiment.

FIG. 5 illustrates a perforated plate, in accordance with an example embodiment., The perforated plate 24 includes a plurality of aligned filaments 51. The filaments 51 may be formed of stainless steel. The filaments 51 are connected to inner walls of the housing 12 so that they span across an entire width of an inner airflow channel extending between the airflow inlet 14 and the airflow outlet 16. In an example embodiment, the perforated plate 24 includes a first row of aligned filaments 52 and a second row of aligned filaments 53, orthogonal to the first row to provide a grid of square apertures 54 between the filaments 51. In other words, the perforated plate 24 is formed from a mesh defining the plurality of apertures 54.

The aerosol generated by the aerosol generator 22 flows through the perforated plate 24. Droplets within the aerosol that are larger than the apertures 54 are blocked by the filaments 51. In this way, the aerosol that exits the airflow outlet 16 does not include any droplets that are larger than the apertures 54.

Figure 6:
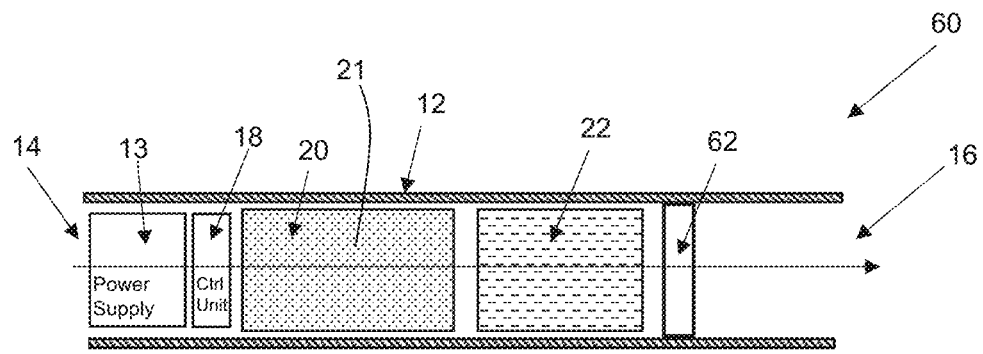
FIG. 6 illustrates a schematic representation of an aerosol generating system, in accordance with an example embodiment.

FIG. 6 illustrates a schematic representation of an aerosol generating system, in accordance with an example embodiment. The second example embodiment includes many of the same elements as the first example embodiment, such as the housing 12 with an airflow inlet 14 and an airflow outlet 16. Like reference numerals are used to designate like parts. Within the housing 12 is a power supply 13 and control unit 18, a reservoir 20 of liquid aerosol-forming substrate 21 and an aerosol generator 22. Either of the configurations of aerosol generator 22 shown in FIGS. 2 to 4 could be used in this second example embodiment of the example embodiments. The second example embodiment of the aerosol generating system 60 further includes an electrode 62. The aerosol generated by the aerosol generator 22 passes over the electrode 62 as the droplets of aerosol flow towards the airflow outlet 16 and the droplets of aerosol are ionized or charged by the electrode 62. The electrode 62 may include at least one of a mesh or a ring or a plate with a central hole through which an aerosol can pass. In this configuration, the aerosol is drawn through the electrode 62 by the airflow from an external force on the system. As the droplets of aerosol pass through the electric field created by the electrode 62 the droplets are ionized. As described herein, the droplets having a diameter above 2 micrometres are charged above their Rayleigh Limit. This ensures that droplets with a diameter above 2 micrometres break apart as the internal electrostatic forces overcome the surface tension.

Figure 7:
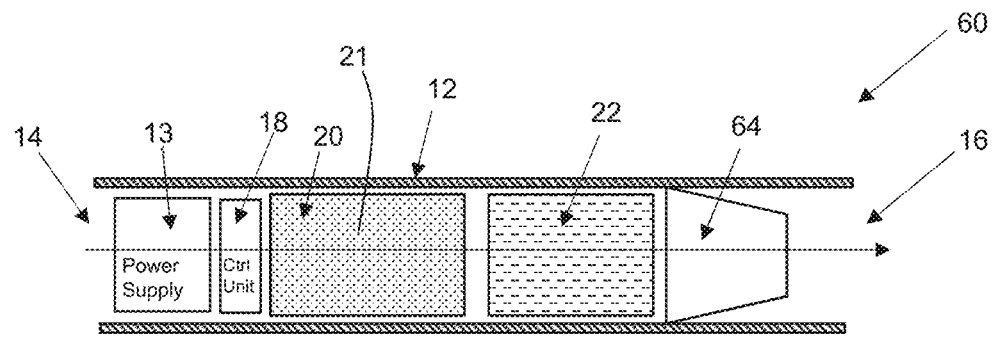
FIG. 7 illustrates a schematic representation an electrode structure, in accordance with an example embodiment.

FIG. 7 illustrates a schematic representation an electrode structure, in accordance with an example embodiment. In one example embodiment, the electrode may be a nozzle 64. All aerosol generated by the aerosol generator 22 must pass through the charged nozzle 64. Therefore all droplets of the aerosol will pass through the centre of the electric field created by the electrode 64. The nozzle 64 directs the charged aerosol towards the airflow outlet 16 to be inhaled. Charging the droplets of the generated aerosol to a predetermined charge, chosen dependent on the liquid aerosol-forming substrate used and known as the Rayleigh Limit, ensures that droplets over a predetermined maximum size break apart as the internal electrostatic repulsive forces overcome the surface tension. Only droplets below the maximum predetermined size exit through the airflow outlet 16 to be inhaled.

In a third example embodiment, the features of the first and second example embodiments are combined.

Figure 8:
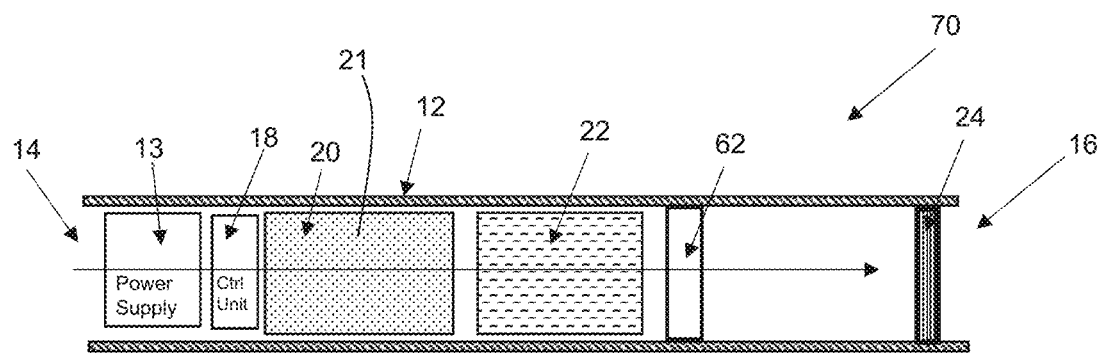
FIG. 8 illustrates a schematic representation of a an aerosol generating system, in accordance with an example embodiment.

FIG. 8 illustrates a schematic representation of a an aerosol generating system, in accordance with an example embodiment.

In an example embodiment, the aerosol is charged by an electrode 62 and also passes through a perforated plate 24 before being inhaled. The perforated plate 24 is electrically grounded with respect to the electrode 62. Droplets charged by the electrode 62 are therefore electrostatically attracted to the perforated plate 24 and accelerate towards the perforated plate 24.

Figure 9:
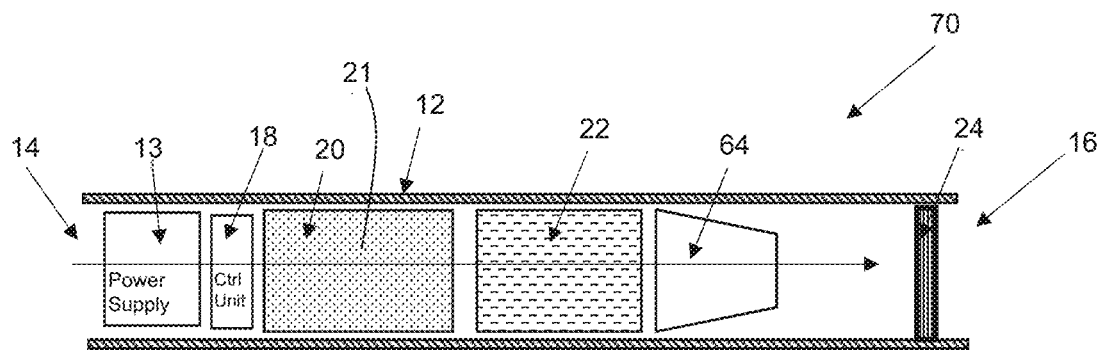
FIG. 9 illustrates a schematic representation of a an aerosol generating system, in accordance with an example embodiment.

FIG. 9 illustrates a schematic representation of a an aerosol generating system, in accordance with an example embodiment.

In an example embodiment, the aerosol is charged by an electrode 64 and also passes through a perforated plate 24 before being inhaled. The perforated plate 24 is electrically grounded with respect to the electrode 64. Droplets charged by the electrode 64 are therefore electrostatically attracted to the perforated plate 24 and accelerate towards the perforated plate 24.

The potential difference between the electrode 62 or 64 and the perforated plate 24, and the distance between the electrode 62 or 64 and the perforated plate are chosen to provide an electrical field that is insufficient to cause electrical breakdown of the air between the electrode 62 or 64 and the perforated plate 24, but may be strong enough to allow droplets with a diameter over 2 micrometres to be charged to above the Rayleigh Limit.

Figure 10:
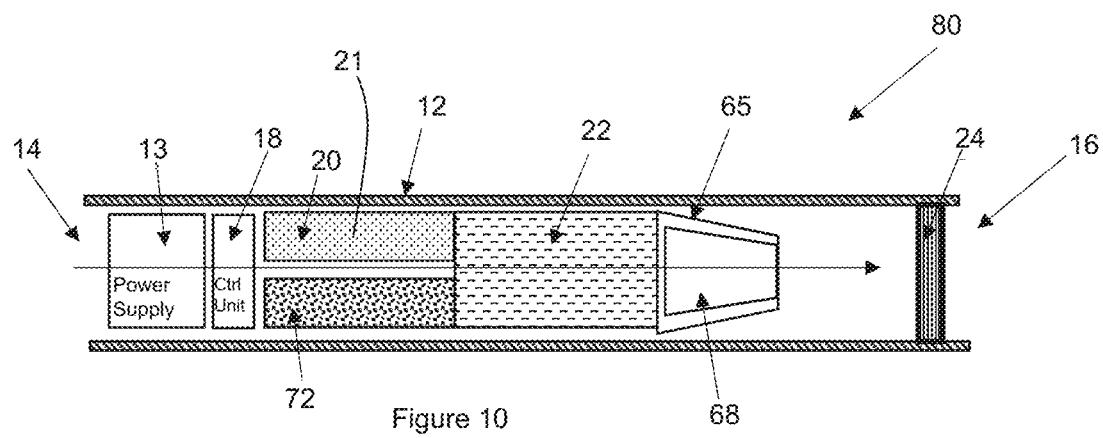
FIG. 10 illustrates a schematic representation of a an aerosol generating system, in accordance with an example embodiment.

FIG. 10 illustrates a schematic representation of a an aerosol generating system, in accordance with an example embodiment. An aerosol generating system 80 may further include a second reservoir 72 disposed within the housing 12. The second reservoir 72 contains an ionizable liquid 73.

Figure 11:
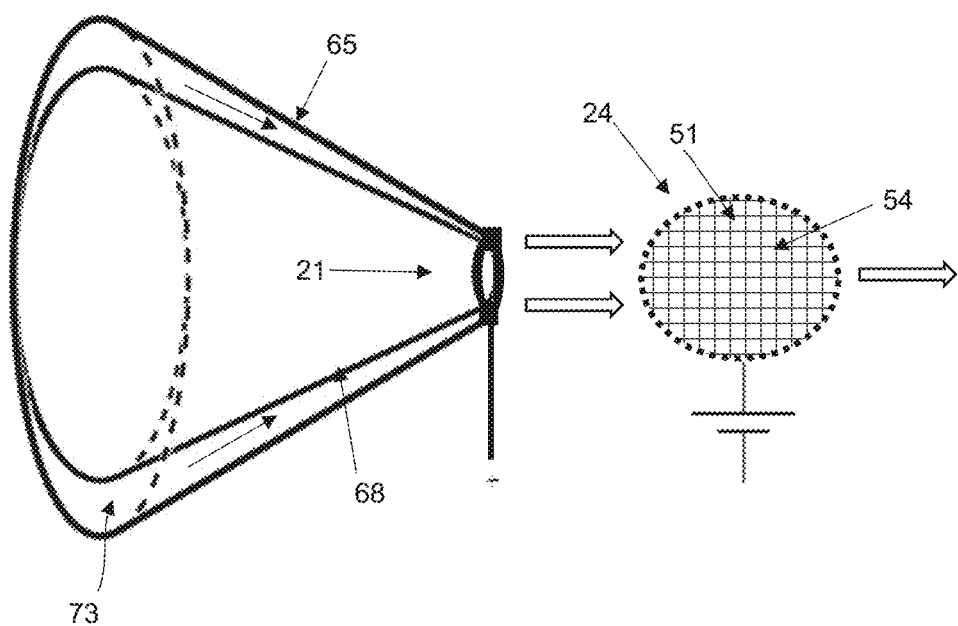
FIG. 11 illustrates a schematic representation of the nozzle configuration of the aerosol generating system of FIG. 10, in accordance with an example embodiment.

FIG. 11 illustrates a schematic representation of the nozzle configuration of the aerosol generating system of FIG. 10, in accordance with an example embodiment. The aerosol generator 22 ejects the liquid aerosol-forming substrate 21 and the ionizable liquid 73, for example, ethanol, through coaxial nozzles 68 and 65 respectively. At least one of the nozzles 65, 68 forms the electrode of this configuration such that the mixture of ionizable liquid and liquid aerosol-forming substrate ejected from the nozzles 65, 68 is ionized. This configuration may improve ionization of a liquid aerosol-forming substrate without an ionizable liquid.

In any of the configurations of the third example embodiment of the aerosol generating system 70, 80, the perforated plate 24 may be connected to the control unit 18 in such a way that any electrical current in the perforated plate 24 can be measured. Alternatively, an electrical current measuring device or circuit can be provided separately from the control unit 18. As charged droplets pass through the perforated plate 24, the droplets impart their charge to the grounded perforated plate 24, which will create a current in the perforated plate 24. Therefore, by measuring the current in the perforated plate 24, the rate of droplets passing through the array can be determined.

The exemplary embodiments described above are not intended to limit the scope of the claims. Other example embodiments consistent with the exemplary embodiments described above will be apparent to those skilled in the art.

The invention claimed is:

1. An aerosol generating system comprising:
   a housing defining an airflow outlet;
   a liquid aerosol-forming substrate;
   an aerosol generator configured to generate an aerosol from the liquid aerosol-forming substrate; and
   an electrode disposed between the aerosol generator and the airflow outlet, the electrode configured to generate an electric field which ionizes droplets of the aerosol such that the droplets over a threshold size break apart into smaller droplets; and
   a ground element downstream of the electrode with respect to the airflow outlet and between the electrode and the airflow outlet, the ground element covering an entire width of the airflow outlet.

2. The aerosol generating system according to claim 1, wherein the ground element is a perforated plate, the perforated plate defining a plurality of apertures extending through the perforated plate.

3. The aerosol generating system according to claim 2, wherein the perforated plate includes a first plurality of parallel filaments and a second plurality of parallel filaments, the first plurality of parallel filaments orthogonal to the second plurality of parallel filaments so that the plurality of apertures is a grid of apertures.

4. The aerosol generating system according to claim 2 wherein a spacing between the electrode and the perforated plate is between 1 millimetre and 50 millimetres.

5. The aerosol generating system according to claim 2, further comprising:
   a control circuit connected to the perforated plate and configured to allow measurement of an electrical current flowing in the perforated plate.

6. The aerosol generating system according to claim 2, wherein the aerosol generating system is configured to generate an electric potential difference between the electrode and the perforated plate.

7. The aerosol generating system according to claim 6, wherein the electric potential difference between the electrode and the perforated plate is between 0.5 kilovolts and 30 kilovolts.

8. An aerosol generating system comprising:
   a housing defining an airflow outlet;
   a liquid aerosol-forming substrate;
   a power supply;
   a controller;
   an aerosol generator configured to generate an aerosol from the liquid aerosol-forming substrate;
   an aerosol charging circuit including a ground element and an electrode arranged for fluid communication with aerosol generated by the aerosol generator, wherein the controller is configured to control a supply of electrical power from the power supply to the electrode to charge the electrode to a potential difference of between 0.5 kilovolts and 30 kilovolts with respect to the ground element, the ground element downstream of the electrode with respect to the airflow outlet and between the electrode and the airflow outlet, the ground element covering an entire width of the airflow outlet.

9. The aerosol generating system according to claim 8, wherein the electrode is a nozzle configured to direct aerosol to the airflow outlet.

10. The aerosol generating system according to claim 8, wherein the ground element is a perforated plate, the perforated plate defining a plurality of apertures extending through the perforated plate.

11. The aerosol generating system according to claim 10, wherein a separation between the electrode and the perforated plate is between 1 millimetre and 50 millimetres.

12. The aerosol generating system according to claim 10, wherein the controller is connected to the perforated plate and configured to measure an electrical current flowing in the perforated plate.

13. The aerosol generating system according to claim 10, wherein the perforated plate includes a first plurality of parallel filaments and a second plurality of parallel filaments, the first plurality of parallel filaments orthogonal to the second plurality of parallel filaments so that the plurality of apertures is a grid of apertures.

14. The aerosol generating system according to claim 8, further comprising:
   a first reservoir containing the liquid aerosol-forming substrate and a second reservoir containing an ionizable liquid.

15. The aerosol generating system according to claim 14, wherein the electrode includes two coaxial nozzles including a first nozzle configured to eject the liquid aerosol-forming substrate from the first reservoir and a second nozzle configured to eject the ionizable liquid from the second reservoir.

* * * * *